United States Patent [19]

Goochee et al.

[11] Patent Number: 5,510,261
[45] Date of Patent: Apr. 23, 1996

[54] METHOD OF CONTROLLING THE DEGRADATION OF GLYCOPROTEIN OLIGOSACCHARIDES PRODUCED BY CULTURED CHINESE HAMSTER OVARY CELLS

[75] Inventors: Charles F. Goochee, San Carlos; Michael J. Gramer, Stanford, both of Calif.

[73] Assignee: The Board of Trustees of the Leland Stanford Juniot University, Stanford, Calif.

[21] Appl. No.: 371,587

[22] Filed: Jan. 12, 1995

Related U.S. Application Data

[63] Continuation of Ser. No. 795,458, Nov. 21, 1991, abandoned.

[51] Int. Cl.$^6$ ............... C12N 5/00; C12P 21/04; A61K 38/16; C07K 14/435
[52] U.S. Cl. .................. 435/240.2; 435/240.3; 435/70.1; 514/8; 530/395
[58] Field of Search ............. 435/240.1, 240.2, 435/240.3, 70.1; 514/8; 530/395

[56] References Cited

PUBLICATIONS

Goochee, C. F., Dev. Biol. Stand., 76:95–104 (1992).
Gramer et al., Abstr. Pap. Am. Chem. Soc., 203 (1–3):BIOT71 (1992).
Andersen et al., Abstr. Pap. Am. Chem. Soc., 203 (1–3):BIOT113 (1992).
Gramer et al., Abstr. Pap. Am. Chem. Soc., 205 (1–2):BIOT168 (1993).
Usuki, et al., *Journal of Biological Chemistry* (Aug. 5, 1988) vol. 263, No. 22:10595–10599.
Sal'Nikova, et al., *Mikrobiologicheskii Zhurnal* (*Kiev*) (1991) vol. 53, No. 6:94–98 (see abstract).
Conzelmann et al., *Advances in Enzymology* (1987) John Wiley & Sons Publishers, pp. 135–150.
Michael W. Spellman et al., "Carbohydrate Structures of Human Tissue Plasminogen Ativator Expressed in Chinese Hamster Ovary Cells" *J. Biol. Chem.* (1989) vol. 264, No. 24, pp. 14100–14111.
Raj B. Parakh et al., "N–Glycosylation and in Vitro Enzymatic Activity of Human Recombinant Tissue Plasminogen Activator Expressed in Chinese Hamster Ovary Cells and a Murine Cell Line" Biochemistry (1989) 28: 7670–7679.
Ernst Conzelmann et al., "Glycolipid and Glycoprotein Degradation" in *Advances in Enzymology*, Ed. Alton Meister, John Wiley & Sons (1987) 60: 89–216.
Seigou Usuki et al., "Sialidase Activities of Cultured Human Fibroblasts and the Metabolism of $G_{M3}$ Ganglioside" *J. Biol. Chem.* (1988) 263: 6847–6853.
Seigo Usuki et al., "Growth Control of Human Foreskin Fibroblasts and Inhibition of Extracellular Sialidase Activity by 2–Deoxy–2,3–dehydro–N–acetyl–neuraminic Acid" J. Biol. Chem. (1988) 263: 10595–10599.
Gramer et al., Biotechnol. Prog., 9(4):366–373 (1993).

*Primary Examiner*—Marian C. Knode
*Assistant Examiner*—Susan M. Dadio
*Attorney, Agent, or Firm*—Cooley Godward Castro Huddleson & Tatum

[57] ABSTRACT

A neuraminidase enzyme with unusually high activity under extracellular culture conditions has been discovered in Chinese hamster ovary (CHO) cells and other types of cells. By affecting the neuraminidase activity of the cell culture, the degradation of glycoprotein oligosaccharides produced by these cultured cells can be controlled.

13 Claims, 7 Drawing Sheets

FIG. 1

*Exoglycosidases and an example substrate:*

1.) Neuraminidase (Sialidase)

2.) β-Galactosidase

3.) β-Hexosaminidase

4.) α-Mannosidase

5.) α-Fucosidase

Vmax, Km & Ki data

| pH | Km for 4MU-NANA (mM) |
|---|---|
| 4.5 | 0.162 ± 0.003 |
| 5.5 | 0.119 ± 0.006 |
| 6.5 | 0.259 ± 0.013 |
| 7.5 | 0.369 ± 0.009 |

| Ki - NANA (mM) | |
|---|---|
| 4.5 | 4.341 ± 0.062 |
| 5.5 | 2.830 ± 0.050 |
| 6.5 | 5.469 ± 0.176 |
| 7.5 | 4.606 ± 0.205 |

| Ki - 2,3-D (micromolar) | |
|---|---|
| 4.5 | 10.569 ± 0.188 |
| 5.5 | 5.514 ± 0.311 |
| 6.5 | 7.241 ± 0.659 |
| 7.5 | 8.552 ± 0.895 |

| pH 4.5 | Vmax (nmol/MM/hr) |
|---|---|
| No Inhibitor | 55.12 ± 0.35 |
| NANA | 59.91 ± 1.32 |
| 2,3-D | 63.16 ± 1.06 |

| pH 5.5 | Vmax (nmol/MM/hr) |
|---|---|
| No Inhibitor | 64.74 ± 1.23 |
| NANA | 68.71 ± 0.98 |
| 2,3-D | 70.10 ± 3.68 |

| pH 6.5 | Vmax (nmol/MM/hr) |
|---|---|
| No Inhibitor | 49.90 ± 1.19 |
| NANA | 52.44 ± 1.53 |
| 2,3-D | 54.98 ± 3.00 |

| pH 7.5 | Vmax (nmol/MM/hr) |
|---|---|
| No Inhibitor | 39.07 ± 0.52 |
| NANA | 41.63 ± 1.57 |
| 2,3-D | 42.14 ± 2.49 |

| pH | Vmax/Km |
|---|---|
| 4.5 | 341 |
| 5.5 | 543 |
| 6.5 | 193 |
| 7.5 | 106 |

METHOD OF CONTROLLING THE DEGRADATION OF GLYCOPROTEIN OLIGOSACCHARIDES PRODUCED BY CULTURED CHINESE HAMSTER OVARY CELLS

ACKNOWLEDGEMENTS

This invention was supported in part by grants from the National Science Foundation under grant No. PYI EET-8857712, and the U.S. Government has rights in this invention arising from this support.

CROSS-REFERENCE TO RELATED APPLICATIONS

This application is a continuation of U.S. application Ser. No. 07/795,458, filed Nov. 21, 1991, now abandoned.

INTRODUCTION

1. Technical Field

This invention is directed generally to the field of glycoprotein production by cell culture, typically culture of genetically engineered cells or hybridomas, and is more specifically directed to techniques used in cell culture to maintain the integrity of the expressed glycoproteins.

2. Background

Although a number of different cell lines are used commercially to produce mammalian proteins by techniques of genetic engineering, Chinese hamster ovary (CHO) cell lines have recently become the cell lines of choice. CHO cells are capable of producing desirable mammalian proteins, such as erythropoietin (EPO), in a form suitable for use as human therapeutics, as, among other reasons, their oligosaccharide structures closely resemble those of human cells.

While the amino acid sequence of a protein is determined with high fidelity by the DNA sequence of its gene, the oligosaccharide structures at a particular glycosylation site in a glycoprotein, such as EPO, can show significant heterogeneity depending on the type of cell and/or the culture and purification conditions used to produce the protein. In the past, most of the focus in the field of genetic engineering was on production of a protein with the appropriate amino acid sequence. However, it has come to be realized that the oligosaccharide portion of a glycoprotein can have a profound effect on properties of the molecule, including solubility, specific activity, resistance to protease attack, resistance to thermal denaturation, circulatory half-life, antigenicity, and immunogenicity. Therefore, attention is currently focused on producing therapeutic glycoproteins which have both native amino acid sequences as well as oligosaccharide structures that enhance therapeutic properties.

Investigators have recently reported differences in the carbohydrate structure of the protein human tissue plasminogen activator (TPA) when expressed in CHO cells. See, for example, Spellman et al., *Journal of Biological Chemistry* (1989) 264:14100–14111, and Parekh et al., *Biochemistry* (1989) 28:7670–7679. The cause of these differences has not been well understood. Such differences are nonetheless very important in the production of therapeutics, since current Food and Drug Administration (FDA) regulations require an invariant process so that the same glycosylation pattern will be obtained during the production of any biological therapeutic.

Figure 1:
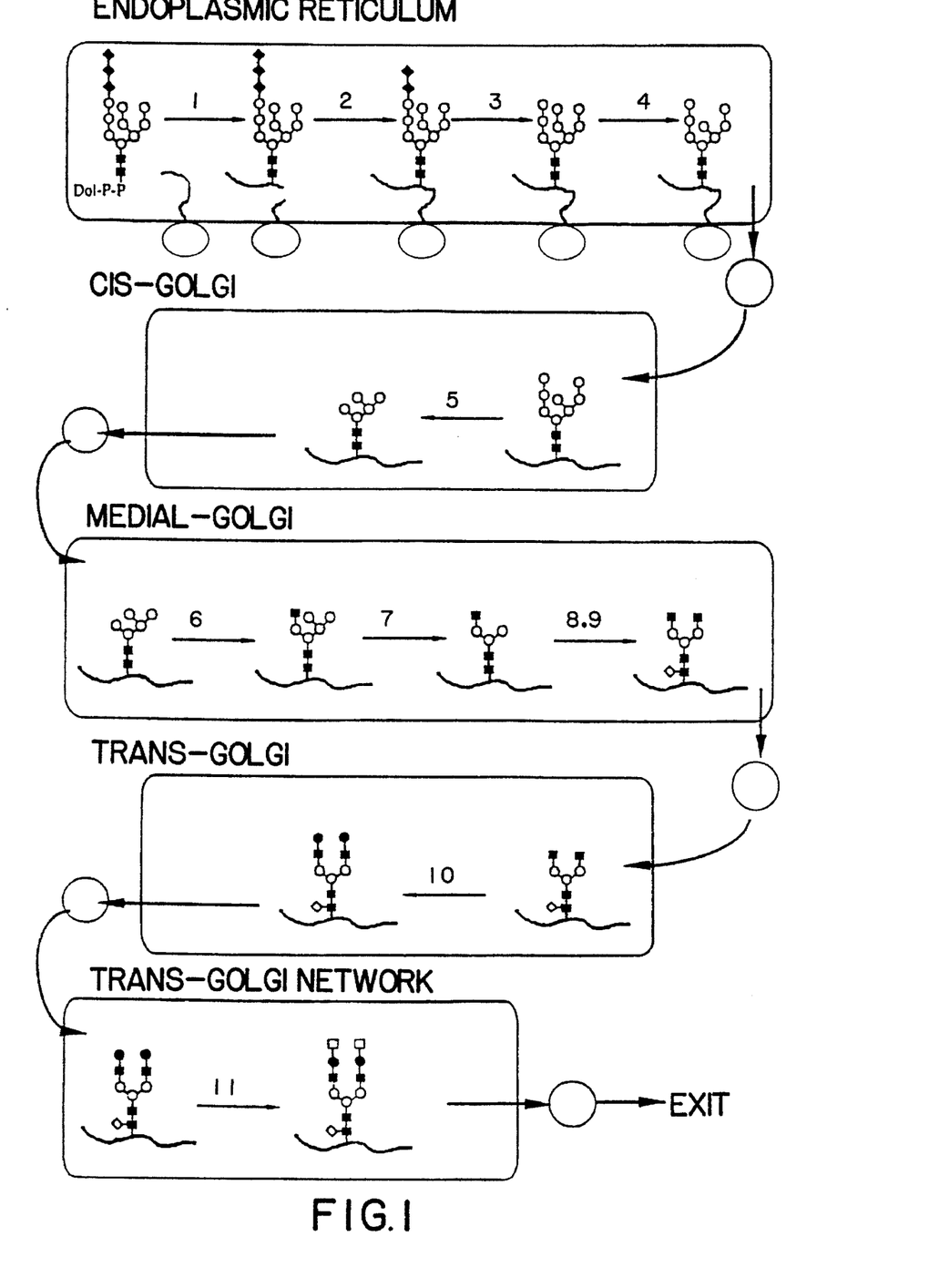
FIG. 1 is a schematic diagram showing a typical oligosaccharide processing pathway of N-linked glycosylated proteins within mammalian cells prior to secretion.
Figure 2:
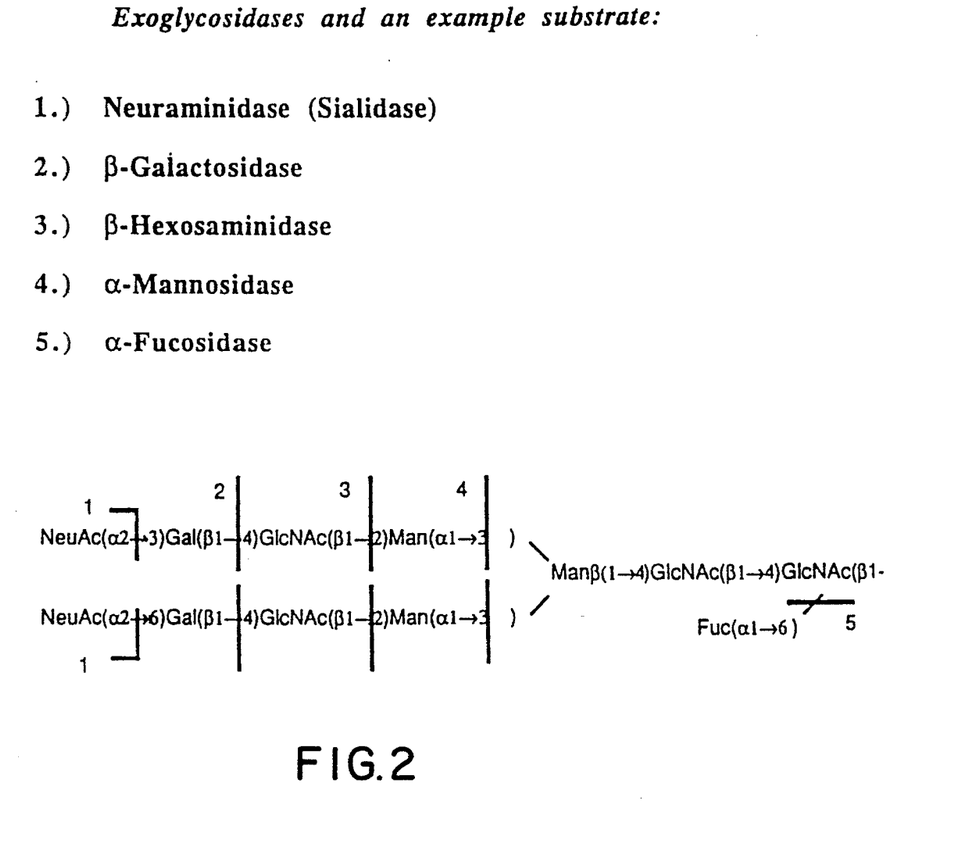
FIG. 2 is a diagram showing typical sites of action of exoglycosidases including neuraminidase on an exemplary oligosaccharide substrate.

Oligosaccharide biosynthesis occurs as the result of a sequence of enzyme catalyzed reactions in several intracellular compartments. Even small differences in an oligosaccharide structure can affect the properties of some glycoproteins. For example, FIG. 1 shows typical oligosaccharide processing for a hypothetical glycoprotein that will be secreted by a cell. While the protein is being synthesized on the ribosome attached to the endoplasmic reticulum, a pre-formed oligosaccharide is transferred from a dolichyl-diphosphate group to an amino acid chain. After a series of enzymatic transformations in the endoplasmic reticulum, the oligosaccharide is transferred to the golgi apparatus for further processing. The typical final product consists of a branched oligosaccharide chain with the principal branches terminating in sialic acid groups attached to penultimate galactose groups.

This terminal sialic acid is often key to the efficacy of the expressed glycoprotein. For example, the absence of terminal sialic acid residues from the oligosaccharides of glycoproteins results in their rapid clearance from the circulatory system, presumably through the asialoglycoprotein receptor of liver cells. This mechanism is apparently responsible for the abolishment of in vivo activity of EPO following removal of sialic acid from its oligosaccharides using a microbial neuraminidase enzyme. In addition, the absence of terminal sialic acid often results in a precipitous decline in glycoprotein solubility, leading to subsequent difficulties in formulation. For a review of glycolipid and glycoprotein degradation, see Conzelmann and Sandhoff, "Glycolipid and Glycoprotein Degradation" in *Advances in Enzymology* (1987) 60: 89–216 (especially pages 135–150, relating to sialidases).

Prior to the present invention, extracellular endogenous neuraminidase activity was not considered to be a significant problem for in the production of human therapeutic proteins using cultured mammalian cells such as CHO cells. No neuraminidase had previously been reported intracellularly or in the external environment of CHO cells or hybridomas, and the properties of the other mammalian neuraminidases that were known were such that significant extracellular activity was not expected to occur. For example, extracellular neuraminidases (sialidases) of fibroblasts have little activity at pH 7 (the normal extracellular environment for cell culture), and further exhibit half lives of only minutes to a few hours at 32° C. See, for example, Conzelman and Sandhoff, *Advances in Enzymology*, (1987) 60:89–216, Usuki et al., *Journal of Biological Chemistry* (1988) 263:6847≧6853, and Usuki et al., *Journal of Biological Chemistry* (1988) 263:10595–10599. Additionally, as reported in the third of these three publications, inhibition of extracellular sialidase (neuraminidase) activity caused a growth inhibitory effect on the cells being cultured, which would be an undesirable property for cells being used for protein production.

The present inventors have discovered the presence of a new neuraminidase in the extracellular medium of CHO cells. This new neuraminidase has significantly different properties from those of previously known neuraminidases including substantial activity above pH 7 and enhanced thermal stability, thus neuraminidase activity can be controlled without adversely affecting cell growth or product integrity. Accordingly, the present invention allows control of extracellular neuraminidase activity during the culture of CHO cells.

SUMMARY OF THE INVENTION

Accordingly, it is the object of the present invention to provide techniques for controlling glycoprotein oligosaccharide structure in CHO and other protein production cells and particularly to eliminate undesired changes in the glycosylation patterns of genetically engineered proteins or those produced by hybridoma cells, especially those that are present in the extracellular culture medium of CHO cells. These and other objects of the invention as will hereinafter become more readily apparent have been accomplished by providing knowledge of the existence of a previously unknown neuraminidase as well as the characteristics of this new neuraminidase, the characteristics being such that neuraminidase activity will be found in CHO and other cell culture media under conditions previously not thought to be conducive to neuraminidase activity. The activity can be controlled by selection of operating conditions and use of neuraminidase inhibitors.

BRIEF DESCRIPTION OF THE DRAWINGS

FIG. 9 at 5.5; FIG. 10 at pH 6.5; FIG. 11 at pH 7.5).

DESCRIPTION OF SPECIFIC EMBODIMENTS

The present invention arises from the discovery of an extracellular neuraminidase activity not previously known to exist in association with Chinese hamster ovary cells and other cell lines used in the production of mammalian proteins by cell culture. Now that this enzyme activity has been identified and characterized, it is possible actively to select conditions for the culturing of CHO and other protein production cells that either increase or decrease this neuraminidase activity at each step of the fermentation and purification processes. By "condition" is meant here any physical, chemical, or biochemical state, such as temperature, pressure, time of culturing, cell line chosen, nutrient present or absent, or biochemical agent (such as an inhibitor) that is present or absent. Thus, it will be possible to control conditions that were previously uncontrolled and to eliminate variations in oligosaccharide structure merely by using standard control processes and the new knowledge of the existence of this previously unknown extracellular neuraminidase activity and its associated properties.

Figure 3:
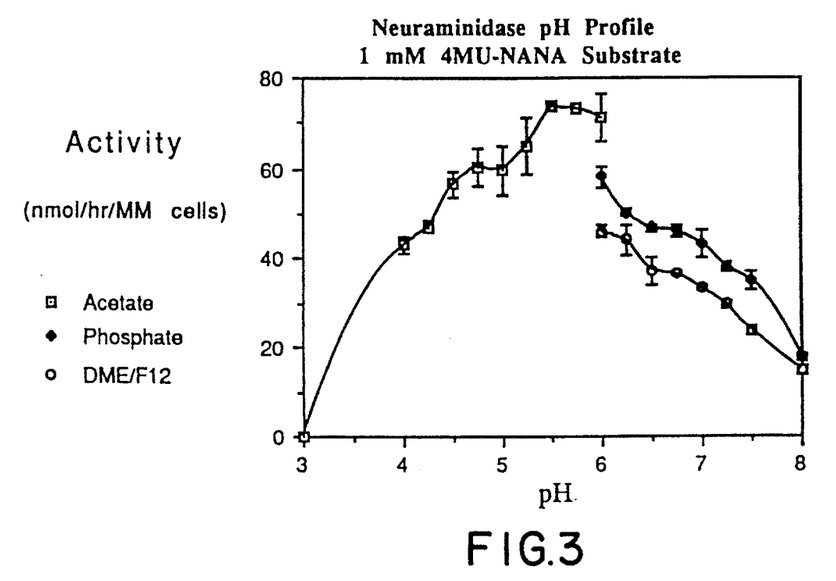
FIG. 3 is a graph showing CHO cell neuraminidase activity versus pH for a model substrate, 4-methyl-umbelliferyl-α-D-N-acetyl-neuraminic acid (4MU-NANA).

Specifically, the inventors have demonstrated that a significant amount of endogenous mammalian neuraminidase activity is present in the extracellular medium during the cultivation of Chinese hamster ovary cells. This activity is enzymatic in nature and is quite stable at 37° C., having a half life of as much as two days at 37° C., which is much greater than that which would be expected for previously known neuraminidase enzymes under extracellular conditions. While the optimum pH for this activity is around 5.5 (see FIG. 3), there is substantial activity at pH 6.5 and higher, particularly near pH 7 where cells are normally cultured. Some previously known neuraminidases also had optimum pH values of around 5.5, but the activity fell off rapidly at higher pH values. Typically these prior neuraminidase had a relative activity at pH 7 of no more than 10 percent of the maximal activity at optimum pH. Thus, preparation of a neuraminidase pH profile, such as that shown in FIG. 3, will readily allow determination of whether a particular neuraminidase belongs to the class of previously known compounds or to the class of compounds described herein. Preferred neuraminidases of the invention have a relative activity at pH 7 compared to optimum activity of at least 25%, more preferably at least 50%. Especially preferred are those neuraminidases that have a pH activity profile such that at any point between pH 3 and 8, the activity relative to optimum activity is within 10% of that shown in FIG. 3. As shown in FIG. 3, absolute values of neuraminidase activity will typically vary with the buffer being used. If possible, activity the optimum pH 5 to pH 7 should be measured in the same buffer. However, relative pH values can be extrapolated from data obtained using different buffers. Relative (if not absolute) activity profiles in different buffers resemble each other over the same range of pH values (as shown in FIG. 3), and it is possible to extrapolate the relative activity from specific activities shown in two different buffer systems. From the activity profile shown in FIG. 3, the relative activity at pH 7 in both phosphate and DME/F12 buffers is in the range of 70–75 percent of the activity of optimum pH (have 5.5). The optimum relative activity that is obtained by assuming that the activity at pH 5.5 (the optimal pH value) is the same relative amount higher than at pH 6.0 in acetate, phosphate, and DME/F12 buffers.

Studies have demonstrated that the neuraminidase activity described herein is a potential cause of at least some of the microheterogeneity of oligosaccharide chains that has been previously described for glycoproteins expressed by genetically engineered CHO cells. Previously there was speculation that the microheterogeneity occurred during synthesis steps. In fact, the present invention is the first demonstration of any neuraminidase activity in CHO cells. Although the reason is unknown, it is possible that the unusual properties of the neuraminidase enzyme that has been discovered by the present inventors has kept this enzyme from previously being discovered. The thermal stability of the CHO-lysate neuraminidase enzyme is several times higher than the most stable mammalian neuraminidase previously reported. Additionally, the range of pH values at which significant activity is present is substantially higher than that reported for other neuraminidases, which have so little activity at pH 7 that extracellular neuraminidase activity was not previously expected to occur.

Based on the present discoveries, it is now possible to minimize degradation of glycoprotein oligosaccharides by neuraminidase from CHO cells and other glycoprotein production lines. Any reduction in activity is desirable when the goal is to preserve oligosaccharide integrity. Conditions that reduce activity by 10, 25, 50, 75, 90, 95, and 99% are increasingly preferred. Complete cessation of neuraminidase activity is most preferred.

Neuraminidase activity can be blocked or reduced in a number of different ways. First, the bioreactor and/or the protein-purification conditions can simply be adjusted to avoid significant degradation by neuraminidase. For a discussion of bioreactor design and the various controls that can be exercised, see Ho and Oldshue (eds.), Biotechnology Processes Scale-Up and Mixing, Am. Inst. of Chem. Engineering, New York, N.Y., and Moody and Baker (eds.) Bioreactors and Biotransformations, Elsevier, London, UK. Neuraminidase release can occur even from healthy cells, so that conditions can be adjusted to avoid such release. Additionally, by harvesting the cell supernatant before there is significant loss of cell viability, release of neuraminidase from lysed cells can be avoided. This contrasts with the typical cell culture conditions for high protein production, which generally stress high concentration of cells with little regard being paid to viability of the cells. Additionally, the process of concentrating of cell culture supernatant before the initial protein purification step can now be seen to increase the concentration of the neuraminidase in the medium and therefore to increase the rate of cleavage of sialic acid residues. Accordingly, neuraminidase activity is minimized during purification by diluting the culture medium (or at least minimizing the concentration process) until after initial purification steps that partially purify the desired protein and/or inactivate the neuraminidase and thus remove some or all of the neuraminidase activity. However, these first two options are not likely to be economically most advantageous, since they will make production of large quantities of protein more difficult. However, some loss of protein production is manageable if balanced by the increased integrity of the material produced, as is provided by the present invention.

Another means for minimizing neuraminidase degradation is to adjust the supernatant pH to somewhat higher levels. As FIG. 3 demonstrates, neuraminidase activity is approximately twice as high at pH 7.0 as it is at pH 8.0. Increases in pH to about 7.5 under culture and/or purification conditions are compatible with cell growth and productivity. When cell viability is of no concern, as in purification steps, pH can rise even higher (e.g., pH 8). An easy technique that can be incorporated into any fermentation process that controls pH by bubbling carbon dioxide through the reaction medium is to purge the reaction medium with nitrogen or another inert gas after fermentation has taken place for the desired length of time. Cessation of carbon dioxide bubbling will immediately raise pH as more ammonium ion is released by the cells into the culture medium.

As an alternative and preferred technique for reducing neuraminidase activity, a neuraminidase inhibitor can be added to the cell culture medium or to any of the downstream processing and/or purification steps. A number of neuraminidase inhibitors are known and can be used in this manner. Likewise, new neuraminidase inhibitors as they are discovered will be useful in the control process described here. Particular inhibitors shown to inhibit the neuraminidase present in CHO cell supernatant include 2,3-dehydro-2-deoxy-N-acetylneuraminic acid (2,3-D) and N-acetylneuraminic acid (NANA).

In its preferred and most narrow meaning, a "neuraminidase inhibitor" is normally considered to be a discreet molecule that either competitively or non-competitively interacts with the active site of the enzyme to reduce the ability of the enzyme to act on its normal substrate. However, in its broadest sense, any chemical or composition that is added to a medium containing neuraminidase activity that results in lowered activity can be said to be an "inhibitor of neuraminidase activity." For example, calcium ions have been shown to be necessary for enzymatic activity for other neuraminidases. Accordingly, a calcium chelating compound such as EDTA, will in effect act as an inhibitor of neuraminidase activity. Although EDTA and similar compounds cannot normally be added to a cell culture medium containing living cells, calcium chelators can be added to the crude or partially purified composition containing glycoproteins in order to reduce neuraminidase activity during the purification process.

Another means for reducing neuraminidase activity is to remove active neuraminidase enzyme from the supernatant during cell cultivation or later processing steps. This can be accomplished in several ways, some examples of which are set out below. Some of these take advantage of the binding of neuraminidase to neuraminic acid (NA) and NA analogs as a consequence of its substrate affinity. An immobilized neuraminic acid analog solid phase (NASP) will preferentially bind neuraminidase compared to other molecules in the culture medium. A NASP can be added to the culture reactor itself, in the form of particles, or can be used in an external column through which supernatant is pumped. Neuraminidase will bind to the NASP and be effectively removed from the glycoprotein substrate, even if physically present in the same culture medium. Neuraminic acid and similar compounds can readily be attached to solid phases uses standard techniques. For example, attachment of sialic acid to a solid support in the form of a column is described in Van Dessel et al., *Journal of Biological Chemistry* (1984) 96:937–947. Additionally β-galactosidase-binding solid supports can be used, since neuraminidase activity is associated with β-galactosidase activity and is also removed by such materials. Columns that bind β-galactosidase activity are available commercially.

Saturated NASP can be regenerated by standard techniques. For example, when an external column is used, the column can be fitted with a heating chamber or manifold which is capable of heating the column to temperatures of 60° C. or higher for brief periodic intervals as the column becomes saturated in order to denature the enzyme. As FIG. 4 indicates, heating at 60° for as little as 20 minutes decreases the activity of neuraminidase by 90%. Higher temperatures will denature enzyme more rapidly. The heating would preferably take place while the column was temporarily disconnected from the fermentor in order to avoid destruction of desired product. Alternative treatments, such as passing a high concentration of NA or an analog through the column to compete with binding to the column and wash neuraminidase into a waste container, could also be used to regenerate the column activity.

A similar means for reducing neuraminidase activity employs an immunoaffinity rather than substrate-affinity solid phase. Antibodies against neuraminidase remove the enzyme from catalytically effective contact with glycoprotein substrate. Antibodies, especially monoclonal antibodies, against neuraminidase can be raised by injecting mammals such as mice, rats, rabbits, or goats with purified or partially purified neuraminidase of the invention according to any of various protocols well known in the art and selecting for antibodies that inhibit neuraminidase activity. The species to which the cell line belongs (e.g., hamsters for CHO cells) is avoided as the immunization host, as is well known. Procedures for producing monoclonal antibodies by hybridoma formation using spleen cells of immunized animals are also well known in the art.

Biological conditions can also be used to minimize supernatant neuraminidase, such as using mutant cell lines deficient in neuraminidase activity. The assay described in the following examples for CHO neuraminidase activity permits rapid visual and/or spectrophotometric screening for neuraminidase-deficient mutant cells from CHO and other cell lines. A similar assay is based on absence of fluorescence released into the supernatant by neuraminidase activity when the fluorescent substrate umbelliferyl-N-acetylneuraminic acid is added. Screening can be performed on plated cells to look for spontaneous mutants. In addition, CHO cells can be incubated with low concentrations of mutagens such as ethylmethanesulfonate, then screened. Procedures for mutagenizing CHO cells are known; see Robbins, *Proc. Natl. Acad. Sci. USA* (1979) 76:1911–1915; Hall et al., *Molec. Cell. Biochem.* (1986) 72:35–45. Preferred mutated CHO cells have at least 10% less extracellular neuraminidase activity at pH 7 than the commercially available cell line CHO-K1 (ATCC CCL 61) when cultured under otherwise identical conditions. Cells in which activity is at least 25, 50, 75, 90, 95, or 99% less than this standard are increasingly more preferred. The most desirable CHO cells have no measurable extracellular neuraminidase activity at pH 7.

Alternatively, antisense DNA can be used to reduce neuraminidase activity. For example, small antisense oligonucleotides can be added to the cell culture medium or the cell line can be made subject to independent dual transfection/selection/amplification of the desired recombinant glycoprotein gene and an antisense gene. Alternatively, the antisense gene can be engineered into the transcribed non-coding regions associated with the amplification or product vectors used in single or co-transfection.

Any condition not specifically described herein can be tested for its effect on extracellular neuraminidases by measuring neuraminidase activity as described herein in the presence and absence of the test condition.

All of the examples described above are generally directed to decreasing extracellular neuraminidase activity however; there are circumstances under which increased extracellular neuraminidase activity would be desirable, such as when removal rather than retention of terminal sialic acid groups is desired. Such conditions are used, for example when the protein is desired not in a form of a glycoprotein but in a form of an asialo-glycoprotein protein.

Figure 5:
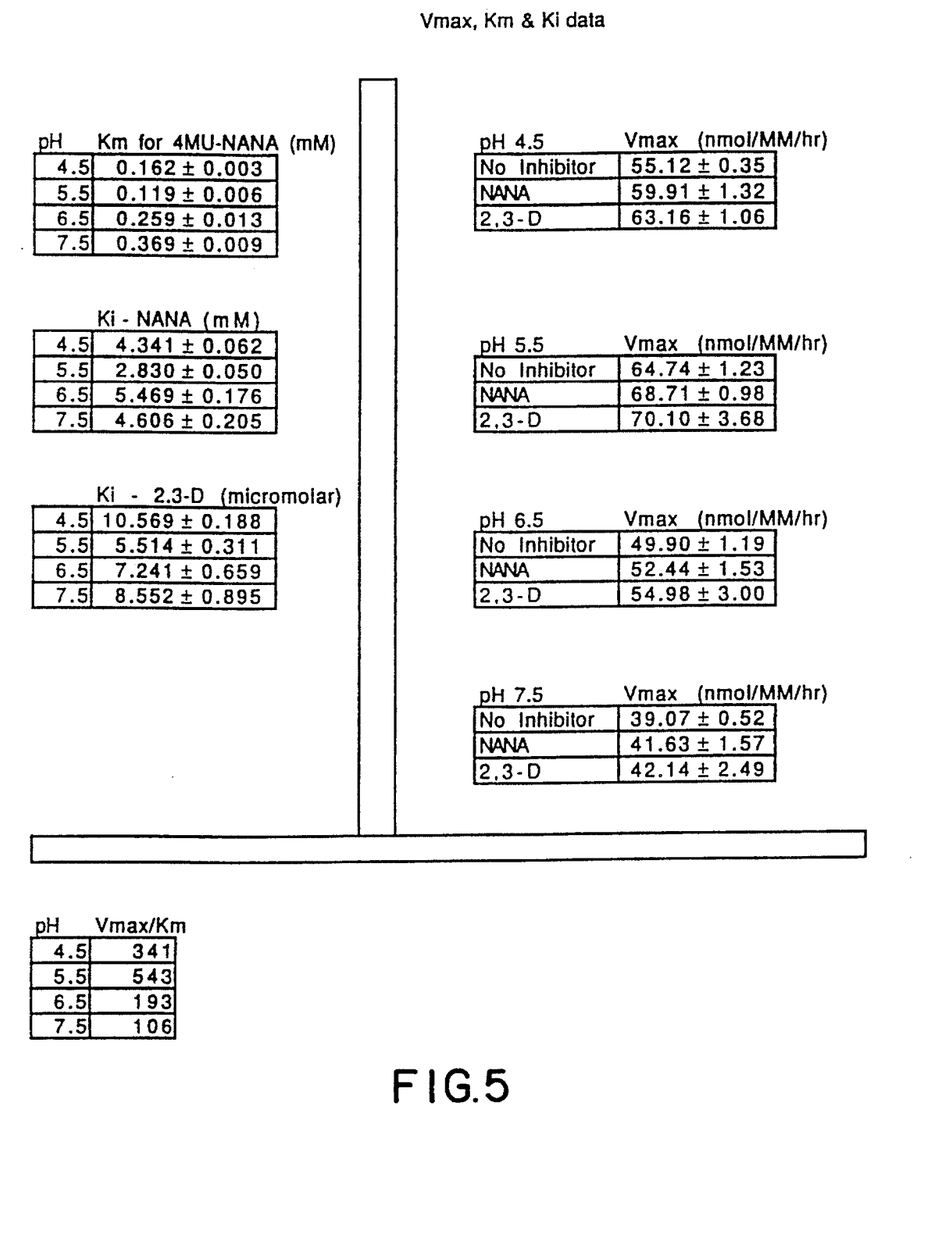
FIG. 5 is a chart showing Vmax, Km, and Ki data obtained as described in the examples that can be used to verify that a neuraminidase obtained from CHO cells is the most preferred CHO neuraminidase of the invention.

In addition to techniques for modifying the extracellular neuraminidase activity, the present invention is also directed to compositions comprising the newly discovered neuraminidase of the invention and to methods for its use. See the examples that follow and FIG. 5, which describes specific identifying characteristics of a particularly preferred CHO neuraminidase of the invention. Although the invention is not limited to this specific enzyme, its properties are illustrative of the newly discovered class of neuraminidases.

Even unpurified compositions containing the neuraminidase of the invention have a number of desirable uses, as is discussed late. For example, since neuraminidase activity is very specific, there is no need to purify compositions in order to carry out studies of inhibitors of neuraminidase. However, in many instances, it will be desirable to at least partially purify the neuraminidase prior to use. Although the extracellular neuraminidase of the invention has so far proven intractable to complete purification, partial purification can be accomplished by passing a CHO culture medium or other source over an immobilized neuraminic acid analog affinity column, which is afterward eluted with excess neuraminic acid. The eluate is size fractionated on a gel permeation column, and the fractions analyzed for activity for example by using the assays described in the following examples. Techniques for purifying other neuraminidases can also be applied to the high pH neuraminidase of the present invention. See, for example, a partial purification of human liver neuraminidase described in Spaltro et al., *Biochemical Journal* (1987) 241:137–143.

Among the many uses of neuraminidase compositions of the invention (even without purification) is the identification and selection of new neuraminidase inhibitors. Prior to the present invention, selection of inhibitors has been difficult because of the poor stability of previously known neuraminidases. Since the compositions of the invention are stable for relatively long periods of time, they readily lend themselves to standard techniques for selecting enzyme inhibitors. The new inhibitors can then by used in the processes described above. When a composition of the invention is purified, neuraminidase specific activity levels (per weight of solid in the composition) are preferably at least twice those of unpurified crude cell suspension, preferably at least ten times higher, more preferably at least fifty times higher.

Additionally, compositions of the invention can be used in methods for selecting neuraminidase inhibitors for use as pharmaceuticals. As with most pharmaceuticals, a key property of desired for is selectivity for the parasite or disease organism whose death or growth inhibition is desired over the host that is being treated. For example, certain viral neuraminidases are known and have been proposed for use in the development of inhibitors against the viral neuraminidases. However, the absence of a readily available mammalian neuraminidase has made selectivity studies difficult if not impossible. The availability of the neuraminidase of the invention allows selectivity studies in which the inhibition of a neuraminidase of a parasite or disease organism is compared to the inhibition by the same test compound of the neuraminidase of the invention. Since most vertebrate neuraminidases, particularly those of mammals and birds, are believed to resemble each other, the availability of the stable neuraminidase of the invention provides an opportunity for testing selectivity that was previously not available. The compositions of the invention are therefore useful in selecting pharmaceutical neuraminidase inhibitors that selectively inhibit disease organism neuraminidases, particularly those of a virus or bacterium.

EXAMPLES

General:

All materials were from Sigma unless otherwise stated. All water used was 18 MΩ from a Milli-Q 5 bowl system (Millipore).

Cells:

The WB1 dihydrofolate reductase mutant (DHFR-) Chinese hamster ovary (CHO) cell line used in reducing the invention to practice was provided by Genentech (South San Francisco, Calif.). Cells were grown by incubation at 37° C. with 5% $CO_2$ in T-flasks (Corning).

Serum supplemented media (SSM) consisted of DME/F12 with glutamine and HEPES, supplemented with an additional 2 mM glutamine (Gibco), 5% fetal bovine serum (Hyclone), antibiotics (100 U/ml penicillin G, 100 µg/ml streptomycen, 25 µg/ml amphotericin B) (Gibco) and GHT (final concentrations: 50 μg/ml glycine, 10 μg/ml hypoxanthine, 10 μg/ml thymidine).

For lysate enzyme assays, confluent cells grown in SSM ($5 \times 10^5$ cells/cm2) were trypsinized and passaged 1:4 into 100 mm tissue culture dishes (Costar) containing 15 ml of SSM. Cells were harvested 1 to 2 days later by first washing twice with 10 ml of cold phosphate buffered saline (PBS: 8 g/l NaCl, 0.2 g/l KCl, 1.13 g/ $Na_2HPO_4$, and 0.2 g/l $KH_2PO_4$, pH 7.5). A third 10 ml aliquot of cold PBS was allowed to sit on the cells for 10 minutes at 4° C. which aided in the loosening of cells from the dish and each other. Cells were removed from the dish with a cell lifter (Costar) and placed in a centrifuge tube. At this time, some cells were removed for cell counts. The remainder of the cells were centrifuged at 100×g for 10 minutes. The PBS was aspirated, and the cells were resuspended in cold water for osmotic lysis at a concentration of $1 \times 10^7$ cells/ml (3.3 mg/ml). Complete disruption was accomplished by passing the cells through a 22 gauge needle five times. Cells were either used fresh for assays, or frozen for future use. All operations above were performed sterilely. Cell counts were performed with a Coulter Multisizer (Coulter Scientific Products) after sufficient pipeting to break up clumps as determined by the cell size distribution profile. Protein concentrations were determined with the BCA kit from Pierce using BSA as a standard.

Artificial Substrate Neuraminidase Assays:

The artificial substrate 2'-(4-methylumbelliferyl)-α-D-N-acetylneuraminic acid (4MU-NANA) was used to assay for neuraminidase activity (modified from Potier et al., Anal. Biochem., 1979, 94, 287). The standard assay for lysate neuraminidase activity contained 0.1M sodium acetate (pH 3–6) or potassium phosphate (pH 6–8) buffer (10 μl of 1 M stock), 1 mM 4MU-NANA (25 μl from a 4 mM aliquot), and the lysate of 0.25 million cells (25 l lysate) in a total volume of 100 μl. Supernatant samples were assayed identically, with supernatant replacing the added cell lysate. The 100 μl samples in plastic 1.5 ml tubes were placed in a 37° C. water bath with a shaker for 30 minutes (sometimes 60 minutes), and the reaction was stopped with 0.9 ml of 0.2M glycine (pH 10.4). The samples were centrifuged at 12,000×g for 15 minutes in a micro centrifuge (Eppendorf) to remove large cellular components, and diluted 10× further into HPLC sample bottles (50 μl sample into 450 μl glycine buffer). An HP 1090 Series II HPLC coupled to an HP 1046A flow through fluorescence detector (Hewlett-Packard) was used for automated sample injection and analysis (no column). The parameters were: injection volume, 25 μl eluant, 0.5 ml/min water; excitation, 365; emission, 448; photomultiplier gain, 10–13; cut-off filter, 370 nm; slit widths, 4×4, 1×1, and 1×1 mm; lamp setting, 1; run time, 0.5 min. The fluorescence was integrated vs. time and compared to standard 4-methylumbelliferyl dilutions. Lysate without substrate, substrate without lysate, and blanks containing only the buffers were used as controls.

Glycoprotein Neuraminidase Assays:

The contents of glycoprotein neuraminidase assays were as above for the artificial substrate, except glycoprotein bound sialic acid was present instead of the artificial substrate (fetuin was from Gibco). The sialic acid released after 4–8 hours was measured by the method of Aminoff (Aminoff, Biochem. J., 1961, 81, 384), scaled down proportionally for a 100 μl sample except that the last step of extraction used less than half the acid butanol called for (400 μl) which more than doubled the sensitivity. The acid butanol phase (220 μl) was transferred to a 96 well plate, and the absorbance was read at 550 nm with a plate reader (Molecular Devices). Controls were as above with the glycoprotein replacing the 4MU-NANA. Sialic acid substrate concentration was measured by release with 0.1N HCl at 80° C. for 50 minutes and quantified by the above method. The absorbance was compared to standard NANA concentrations subjected to the same conditions.

Figure 6:
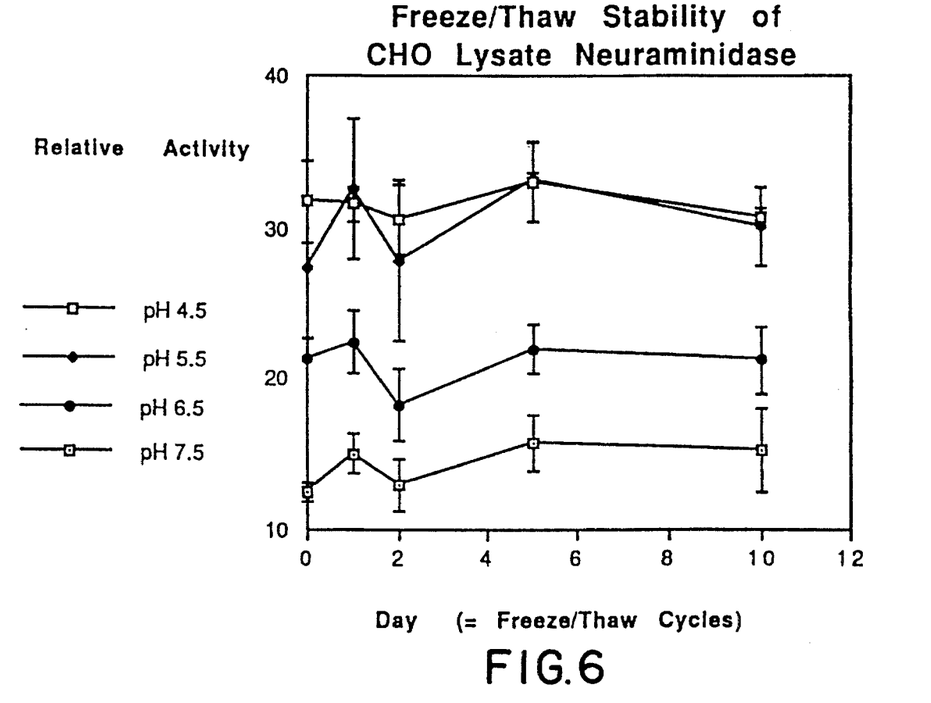
FIG. 6 is a graph showing freeze/thaw stability of CHO lysate neuraminidase at different pH values.

Freeze/Thaw Stability (FIG. 6):

Cells were harvested, disrupted, and aliquotted as stated above. One aliquot was used to measure the 4MU-NANA activity in the freshly harvested cells under standard assay conditions at pH 4.5, 5.5, 6.5 and 7.5, and the rest were frozen at −20° C. Every day thereafter to 10 days, the cells were thawed at 37° C. for 15 minutes, and refrozen. On selected days (1, 2, 5, and 10), one aliquot was used to assay for neuraminidase activity as stated above.

Figure 4:
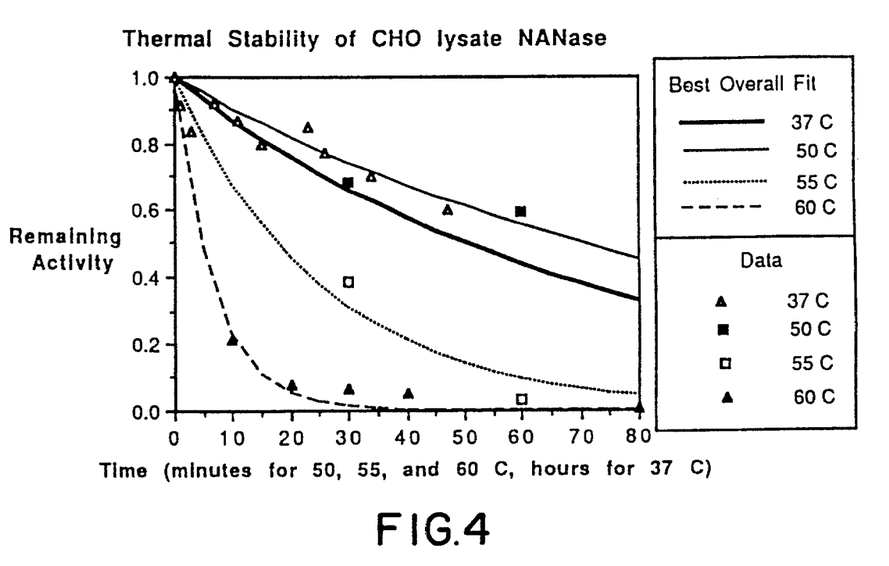
FIG. 4 is a graph showing CHO cell lysate neuraminidase stability, expressed as remaining fractional activity at 37°, 50°, 55°, and 60° C., versus time in hours (37° C.) or minutes (50°, 55°, 60°) for pH 4.5, 5.5, 6.5, and 7.5.

Thermal Stability (FIG. 4):

An aliquot of previously frozen and disrupted cells was thawed at 37° C. and assayed for neuraminidase activity with 4MU-NANA at that temperature and pH 4.5, 5.5, 6.5 and 7.5. Other aliquots were first thawed identically, placed in a water bath at various temperatures (37°, 50°, 55°, and 60° C.) for various times, quenched in an ice bath, and reheated to 37° C. for neuraminidase assay at the four pH[8] mentioned above (thermal stability data at 37° C. was from a different lot of cells assayed only at pH 4.5 and 6.5).

Figure 7:
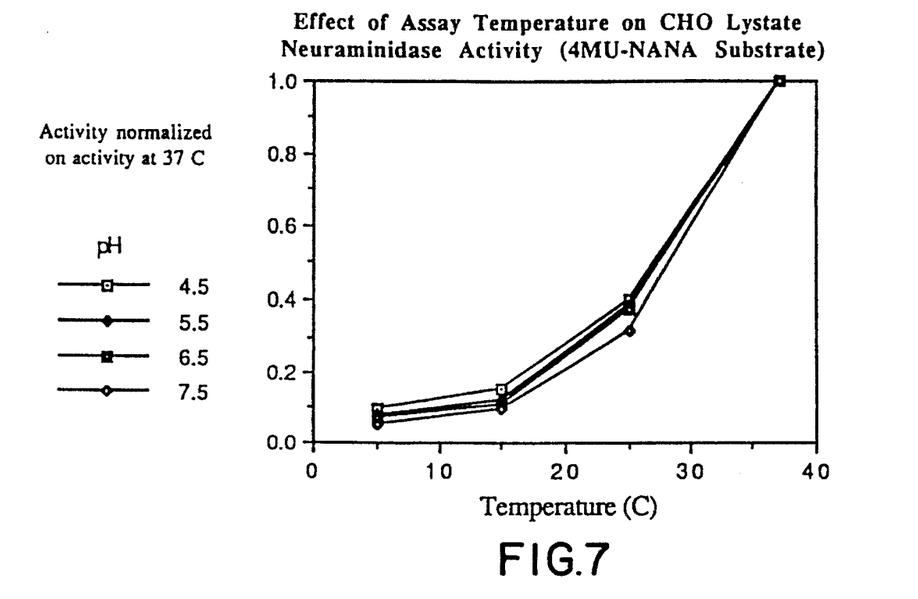
FIG. 7 is a graph showing effect of assay temperature on CHO lysate neuraminidase activity at different pH values.
Figure 8:
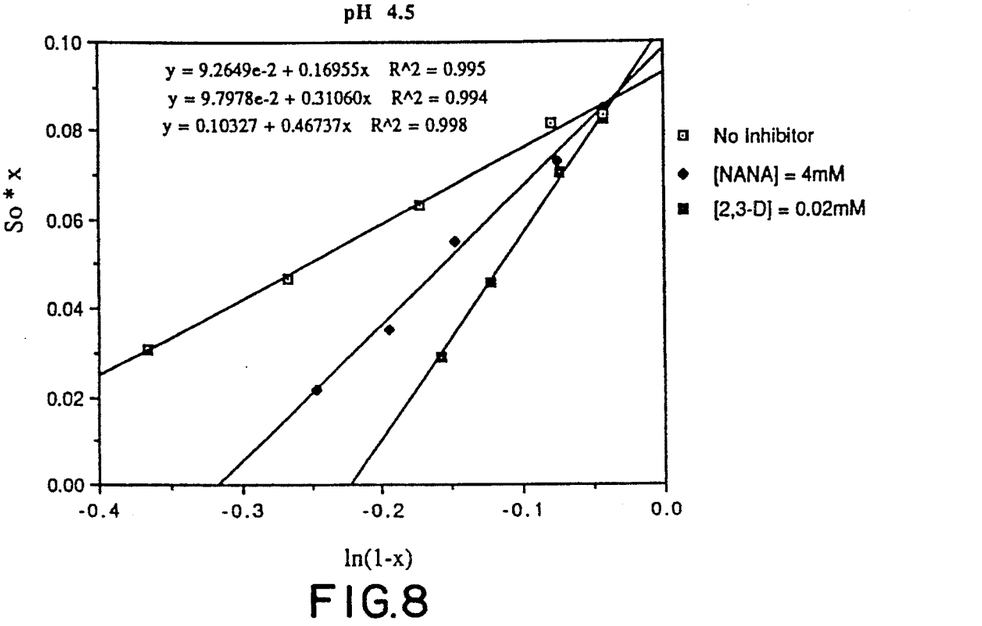
FIGS. 8–11 are a series of four graphs showing effects of substrate and inhibitor concentration on activity at different pH values (FIG. 8 at pH 4.5.
Figure 9:
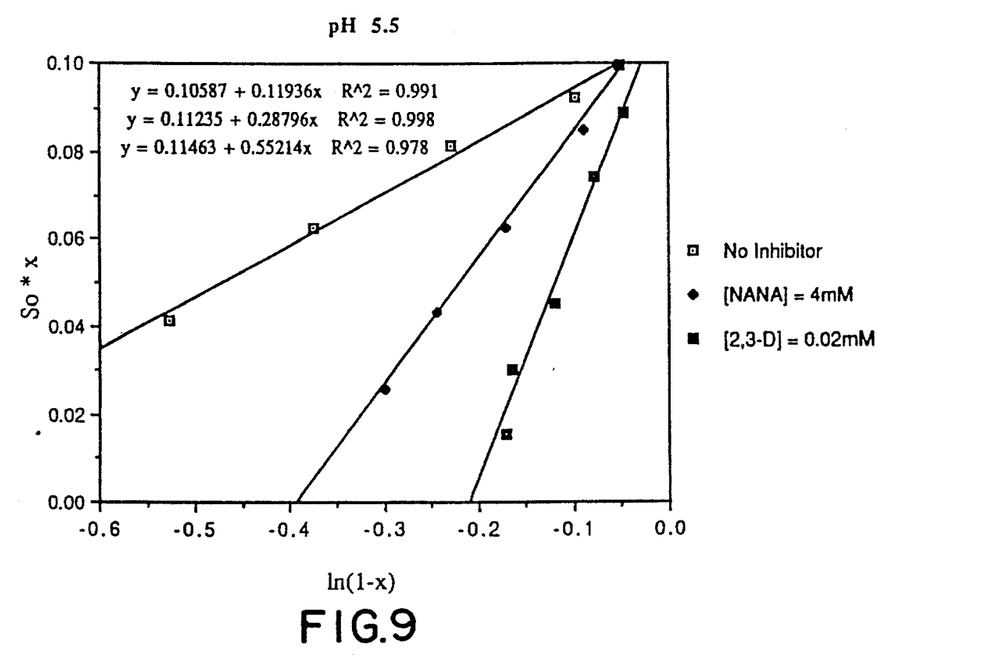
Figure 10:
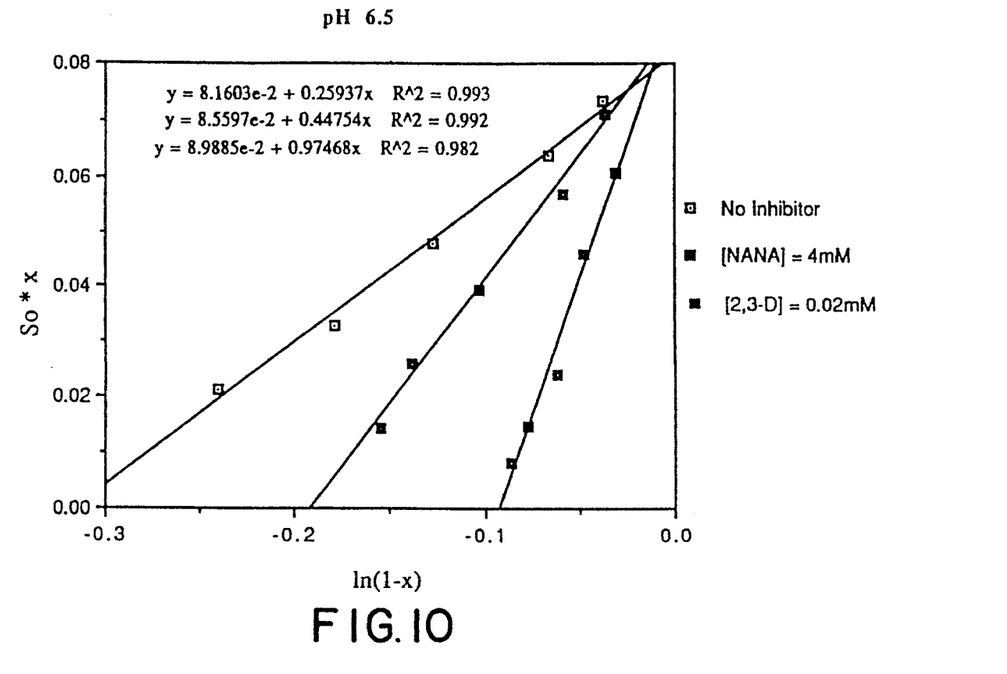
Figure 11:
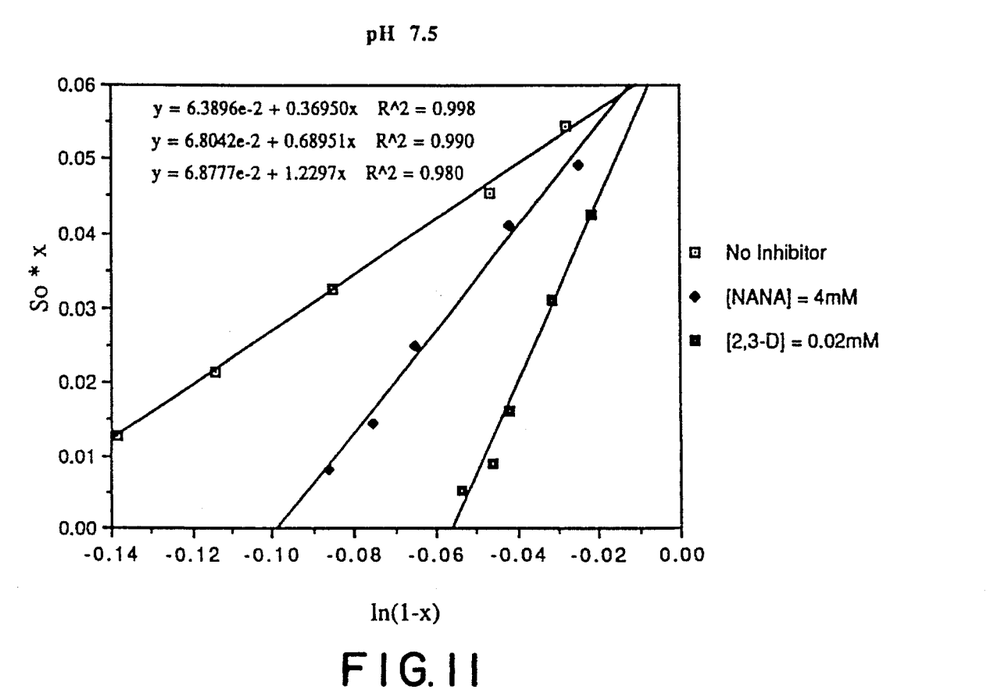

Effect of Temperature (FIG. 7):

Aliquots of previously frozen and disrupted cells were thawed to various temperatures (15°, 20°, 25°, and 37° C.) and assayed at that temperature for neuraminidase activity with 4MU-NANA as in the standard assay at pH 4.5, 5.5, 6.5 and 7.5.

Effect of Substrate and Inhibitor Concentration (FIGS. 8–11):

Aliquots of previously frozen and disrupted cells were thawed to 37° C. and assayed for neuraminidase activity as in the standard assay except the 4MU-NANA concentration varied at 0.1, 0.2, 0.4, 1 and 2 mM (pH 4.5, 5.5, 6.5 and 7.5). Inhibition studies were conducted identically except for the presence of inhibitors: 4 mM NANA; or 20 μM 2,3-D. The effect of bound sialic acid concentration in the form of the glycoprotein substrates was performed in the same manner, except the lysate was incubated with bound sialic acid at concentrations of 0.5, 0.6, 0.7, 0.9, and 1.0 mM pH 5.5 for 4 hours. For pH 4.5, 6.5, and 7.5, the concentration used were 0.5 and 1.5 mM with incubations of 8 hours. Kinetic parameters were determined by fitting an integrated form of the Michaelis-Menton equation:

$$P = Vmax * t + Km * \ln[1-x]$$

Where:

P=Released sialic acid (mM)

x=fraction of hydrolyzed substrate

Km=Michaelis constant (mM)

Vmax=maximum enzymatic rate of saturation (mM/hr)

t=time of reaction (hr)

P was plotted vs+ln[1−x] with the slope=Km and the intercept=Vmax * t. For samples with inhibitor, Ki (inhibitor constant, mM) was calculated as Ki=[1]/(Km,app/Km−1) where [1]=inhibitor concentration (mM), Km,app=the apparent Km with inhibitor added (mM), and Km is the Michaelis constant determined without the inhibitor.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An in vitro method of controlling the degradation of glycoprotein oligosaccharides produced by cultured Chinese hamster ovary (CHO) cells, said method comprises:

culturing CHO cells in a culture medium under conditions selected to increase or decrease the culture's extracellular neuraminidase activity; thereby maintaining or decreasing the sialic acid content of said glycoprotein oligosaccharides.

2. The method of claim 1 wherein said conditions are selected to decrease the culture's extracellular neuraminidase activity.

3. The method of claim 2 wherein said selected conditions comprise culturing said CHO cells in a culture medium comprising a neuraminidase inhibitor.

4. The method of claim 3, wherein said neuraminidase inhibitor is 2,3-dehydro- 2-deoxy-N-acetylneuraminic acid (2,3,-D).

5. The method of claim 3, wherein said neuraminidase inhibitor is N-acetylneuraminic acid (NANA).

6. The method of claim 2, wherein said conditions comprise removing neuraminidase from said culture medium during or after cell culturing.

7. The method of claim 1 wherein said conditions are selected to increase the culture's extracellular neuraminidase activity.

8. An in vitro method of controlling the degradation of glycoprotein oligosaccharides produced by cultured Chinese hamster ovary (CHO cells, said method comprises:

(a) culturing CHO cells in a culture medium; and (b) decreasing the culture's extracellular neuraminidase activity, thereby maintaining the sialic acid content of said glycoprotein oligosaccharides.

9. The method of claim 8, wherein step (b) occurs during or after purification of said glycoprotein oligosaccharides.

10. The method of claim 9, wherein step (b) occurs during purification of said glycoprotein oligosaccharides.

11. The method of claim 8, wherein the culture's extracellular neuraminidase activity is decreased by adding a calcium chelating compound to the culture medium.

12. The method of claim 11, wherein said chelating compound is EDTA.

13. The method of claim 8, wherein said method further comprises diluting said culture medium before or during purification of said glycoprotein oligosaccharides.

* * * * *